United States Patent
Tanabe et al.

(10) Patent No.: US 8,187,230 B2
(45) Date of Patent: May 29, 2012

(54) INDWELLING NEEDLE ASSEMBLY AND METHOD OF USING THE SAME

(75) Inventors: Hidenori Tanabe, Yamanashi-ken (JP);
Ryoji Kobayashi, Yamanashi-ken (JP);
Takato Murashita, Yamanashi-ken (JP)

(73) Assignee: Terumo Kabushiki Kaisha, Shibuya-Ku (JP)

( * ) Notice: Subject to any disclaimer, the term of this patent is extended or adjusted under 35 U.S.C. 154(b) by 0 days.

(21) Appl. No.: 12/868,347

(22) Filed: Aug. 25, 2010

(65) Prior Publication Data
US 2011/0054402 A1 Mar. 3, 2011

(51) Int. Cl.
*A61B 17/34* (2006.01)
(52) U.S. Cl. .................................. 604/164.01; 604/162
(58) Field of Classification Search .................. 604/158, 604/162, 164.01, 164.03, 164.04, 164.07, 604/164.08, 165.01–165.02, 167.01–167.04, 604/167.06, 168.01, 171, 174, 180, 192, 604/195, 263, 264, 272
See application file for complete search history.

(56) References Cited

U.S. PATENT DOCUMENTS

| | | | | |
|---|---|---|---|---|
| 3,903,887 A * | 9/1975 | Antoshkiw | | 604/272 |
| 4,475,548 A * | 10/1984 | Muto | | 128/207.14 |
| 4,512,766 A * | 4/1985 | Vailancourt | | 604/167.03 |
| RE34,416 E * | 10/1993 | Lemieux | | 604/164.01 |
| 5,407,434 A * | 4/1995 | Gross | | 604/167.02 |
| 5,584,809 A * | 12/1996 | Gaba | | 604/110 |
| 5,601,536 A * | 2/1997 | Crawford et al. | | 604/263 |
| 5,810,785 A * | 9/1998 | Bogert et al. | | 604/264 |
| 5,911,705 A * | 6/1999 | Howell | | 604/110 |
| 6,224,569 B1 * | 5/2001 | Brimhall | | 604/164.08 |
| 6,749,588 B1 | 6/2004 | Howell et al. | | |
| 2006/0106348 A1* | 5/2006 | Lichtenberg | | 604/164.08 |
| 2007/0038188 A1* | 2/2007 | Bialecki et al. | | 604/164.08 |

* cited by examiner

*Primary Examiner* — Quynh-Nhu H Vu
(74) *Attorney, Agent, or Firm* — Buchanan Ingersoll & Rooney PC

(57) ABSTRACT

An indwelling needle assembly, including an inner needle having a sharp needle point at a distal end thereof; an inner needle hub which is fixed to a proximal portion of the inner needle and which has a proximal end face; a hollow outer needle into which the inner needle is inserted; and an outer needle hub fixed to a proximal portion of the outer needle, the inner needle is adhered and fixed to the inner needle hub with an adhesive at a proximal portion thereof, and the inner needle hub is provided with a projected part formed by projecting the adhesive toward a proximal side relative to the proximal end face.

6 Claims, 12 Drawing Sheets

INDWELLING NEEDLE ASSEMBLY AND METHOD OF USING THE SAME

CROSS-REFERENCE TO RELATED APPLICATION

This application is based upon and claims the benefit of priority from Japanese Patent Application No. 2009-196829 filed on Aug. 27, 2009, of which the contents are incorporated herein by reference.

BACKGROUND OF THE INVENTION

1. Field of the Invention

The present invention relates to an indwelling needle assembly to be used to puncture a blood vessel and be left indwelling there, in the case of an infusion, for example.

2. Description of the Related Art

At the time of carrying out an infusion on a patient or in other similar situations, an indwelling needle to be connected with an infusion line is made to puncture a patient's blood vessel and is left indwelling for performing the infusion.

Such an indwelling needle assembly, normally, includes a hollow outer needle, an outer needle hub secured to a base end (proximal end) of the outer needle, an inner needle which is inserted into the outer needle and which has a sharp needle point at a tip (distal end) thereof, an inner needle hub secured to a base end (proximal end) of the inner needle, and a protector which is detachably coupled to the outer needle hub. The outer needle hub is formed with a main pipe having a flow path communicating with the lumen of the outer needle, and a side pipe having a branch flow path branched from the flow path in the main pipe, wherein an infusion line is to be connected to the side pipe (see, for example, U.S. Pat. No. 6,749, 588).

At the time of puncturing a patient's blood vessel with the indwelling needle, a puncturing operation is conducted in an assembled condition wherein the inner needle is inserted into the outer needle and the needle point of the inner needle protrudes from the tip (distal end) of the outer needle.

When the needle point of the inner needle has reached the inside of the blood vessel, blood flows into the inner needle through its distal portion, the blood, in its course of flowing, flows through a hole formed in a side portion of the inner needle into a flow path between the outer needle and the inner needle, then flows through the flow path into the inside of the transparent outer needle hub, that is, into the flow path in the main pipe and, further, flows from the main pipe into the branch flow path in the side pipe (flashback). This permits a clinician (user) to confirm (visually recognize) that the inner needle has captured (securely punctured) the blood vessel.

After flashback is confirmed, the outer needle is advanced using the inner needle as a guide, and the outer needle is made to puncture the blood vessel.

Next, while fixing the outer needle or the outer needle hub by holding it by one hand, the inner needle hub is held by the other hand and moved in the proximal direction, to draw the inner needle out of the outer needle. Then, an infusion agent is administered through the connected infusion line, the side pipe of the outer needle hub, the main pipe of the outer needle hub, and the outer needle.

Meanwhile, at the time of putting the outer needle of the indwelling needle assembly indwelling in a patient, the clinician (user) wears gloves, holds the indwelling needle assembly with fingers of the gloved hand, and performs the puncturing operation. In the case of the puncturing operation, the clinician may hold the indwelling needle assembly by a method as shown in FIG. 3, for example.

This holding method is herein referred to as "wing port holding." In this holding method, the thumb is put in contact with the proximal end of the inner needle hub, whereas one of the remaining fingers, for example, the middle finger is put in contact with the distal side of the indwelling needle assembly, specifically, a wing of the outer needle hub, whereby the indwelling needle assembly is held so as to be pinched in the longitudinal direction thereof.

In an indwelling needle assembly according to the related art, however, fingers of a gloved hand are liable to slip relative to the indwelling needle assembly at the time of a puncturing operation. Particularly, the thumb is liable to slip off a base portion (proximal portion) of the inner needle hub, which makes the puncturing operation difficult to achieve.

SUMMARY OF THE INVENTION

An object of the present invention is to provide an indwelling needle assembly which is less liable to slipping and, hence, permits a puncturing operation therewith to be carried out easily.

The above object can be attained by the present invention as represented by the following.

An embodiment of the present invention provides an indwelling needle assembly including:

an inner needle having a sharp needle point at a distal end thereof;

an inner needle hub which is fixed to a proximal portion of the inner needle and which has a proximal end face;

a hollow outer needle into which the inner needle is inserted; and an outer needle hub fixed to a proximal portion of the outer needle, wherein the inner needle is adhered and fixed to the inner needle hub with an adhesive at a proximal portion thereof, and the inner needle hub is provided with a projected part formed by projecting the adhesive toward a proximal side relative to the proximal end face.

In the indwelling needle assembly according to the embodiment of the present invention, the inner needle hub has an inner needle hub body part provided with a recess which opens toward the proximal side and which is filled with the adhesive, and the projected part is protuberant at a central portion of an opening of the recess.

In the indwelling needle assembly according to the embodiment of the present invention, the inner needle hub has an inner needle hub body part provided with a recess which opens toward the proximal side and which is filled with the adhesive, and the projected part is protuberant from the whole area of an opening of the recess.

In the indwelling needle assembly according to the embodiment of the present invention, the proximal end face and the projected part of the inner needle hub constitute a finger hold to be contacted by a thumb of a hand holding the indwelling needle assembly.

In the indwelling needle assembly according to the embodiment of the present invention, the inner needle hub has an inner needle hub body part provided with a recess which opens toward the proximal side and which is filled with the adhesive, the inner needle hub body part is provided at a proximal end face thereof with an annular body which surrounds an opening of the recess and which projects in the proximal direction, and the projected part projects from inside the annular body toward the proximal side relative to a proximal end face of the annular body.

In the indwelling needle assembly according to the embodiment of the present invention, the indwelling needle assembly is used by holding it with fingers of a gloved hand.

In the indwelling needle assembly according to the embodiment of the present invention, the adhesive, after cured, is not slippery on the glove.

A method of using an indwelling needle assembly according to the embodiment of the present invention includes the steps of:

preparing an indwelling needle assembly including an inner needle having a sharp needle point at a distal end thereof, an inner needle hub which is fixed to a proximal portion of the inner needle and which has a proximal end face, a hollow outer needle into which the inner needle is inserted, and an outer needle hub fixed to a proximal portion of the outer needle, the inner needle being adhered and fixed to the inner needle hub with an adhesive at a proximal portion thereof, and the inner needle hub being provided with a projected part formed by projecting the adhesive toward the proximal side relative to the proximal end face;

putting a thumb of a hand in contact with the projected part of the indwelling needle assembly in an assembled condition wherein the inner needle is inserted into the outer needle and the needle point of the inner needle is set protruding from the distal end of the outer needle, putting one of the remaining fingers in contact with the distal side of the indwelling needle assembly, and thereby holding the indwelling needle assembly in the manner of pinching the indwelling needle assembly in the longitudinal direction thereof; and puncturing a living body with the inner needle and the outer needle.

The method of using the indwelling needle assembly according to the embodiment of the present invention, preferably, includes a step of wearing gloves.

According to the embodiment of the present invention, the projected part formed from the adhesive makes it possible, for example, to prevent the thumb of the hand holding the indwelling needle assembly from slipping off the proximal end face of the inner needle hub. This ensures that the puncturing operation can be carried out easily and safely. Particularly, this effect is highly exhibited where the indwelling needle assembly is used by holding it with fingers of a gloved hand.

In addition, as the adhesive for forming the projected part, a portion of the adhesive used in adhering and fixing the proximal portion of the inner needle to the inner needle hub is used. Therefore, the indwelling needle assembly is simple in configuration, and the indwelling needle assembly can be manufactured without especially increasing the number of manufacturing steps.

DESCRIPTION OF THE PREFERRED EMBODIMENTS

Now, an indwelling needle assembly according to the present invention will be described in detail below, based on preferred embodiments shown in the accompanying drawings.

<First Embodiment>

Figure 1:
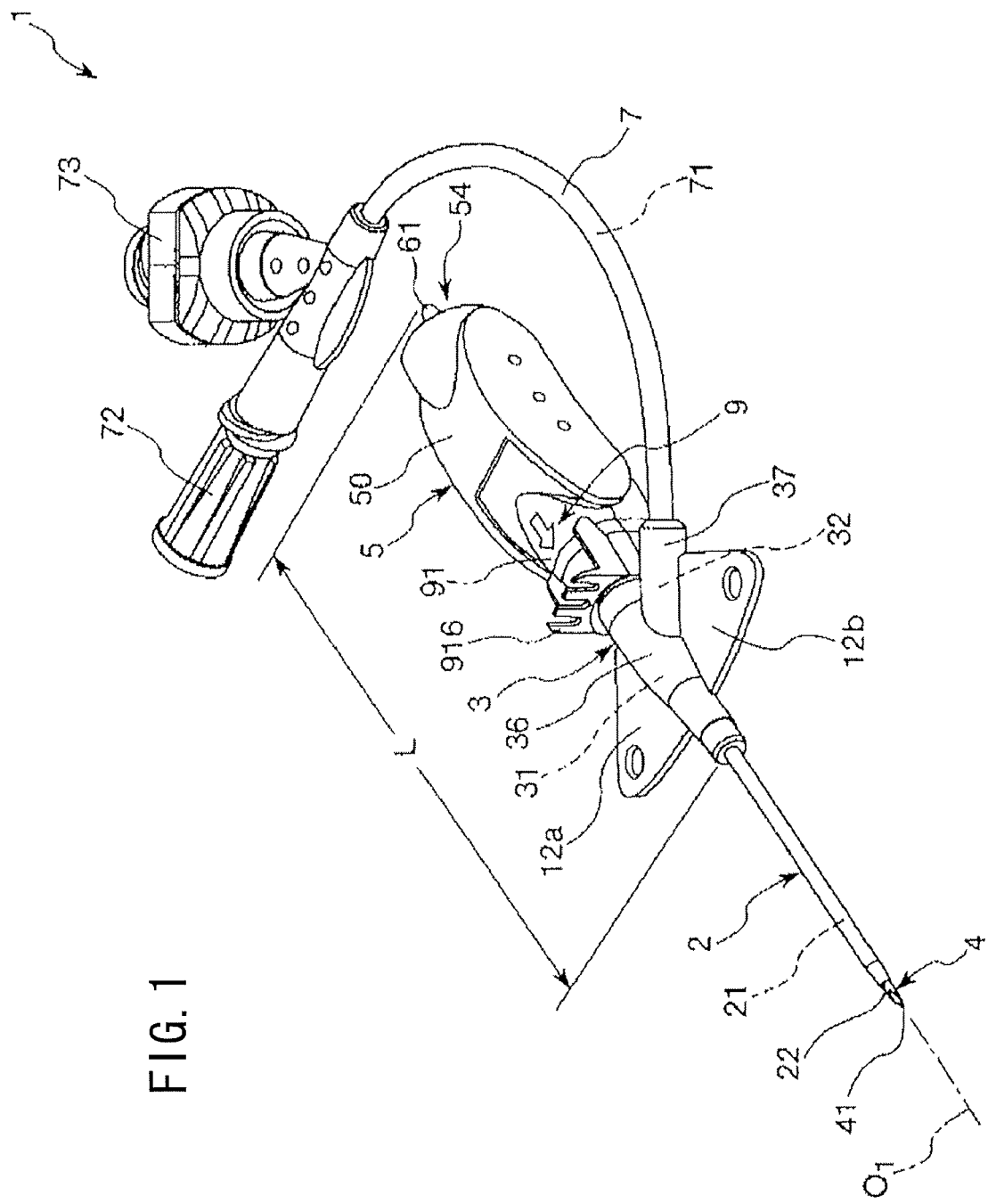
FIG. 1 is a perspective view showing an embodiment of the indwelling needle assembly according to the present invention.
Figure 2:
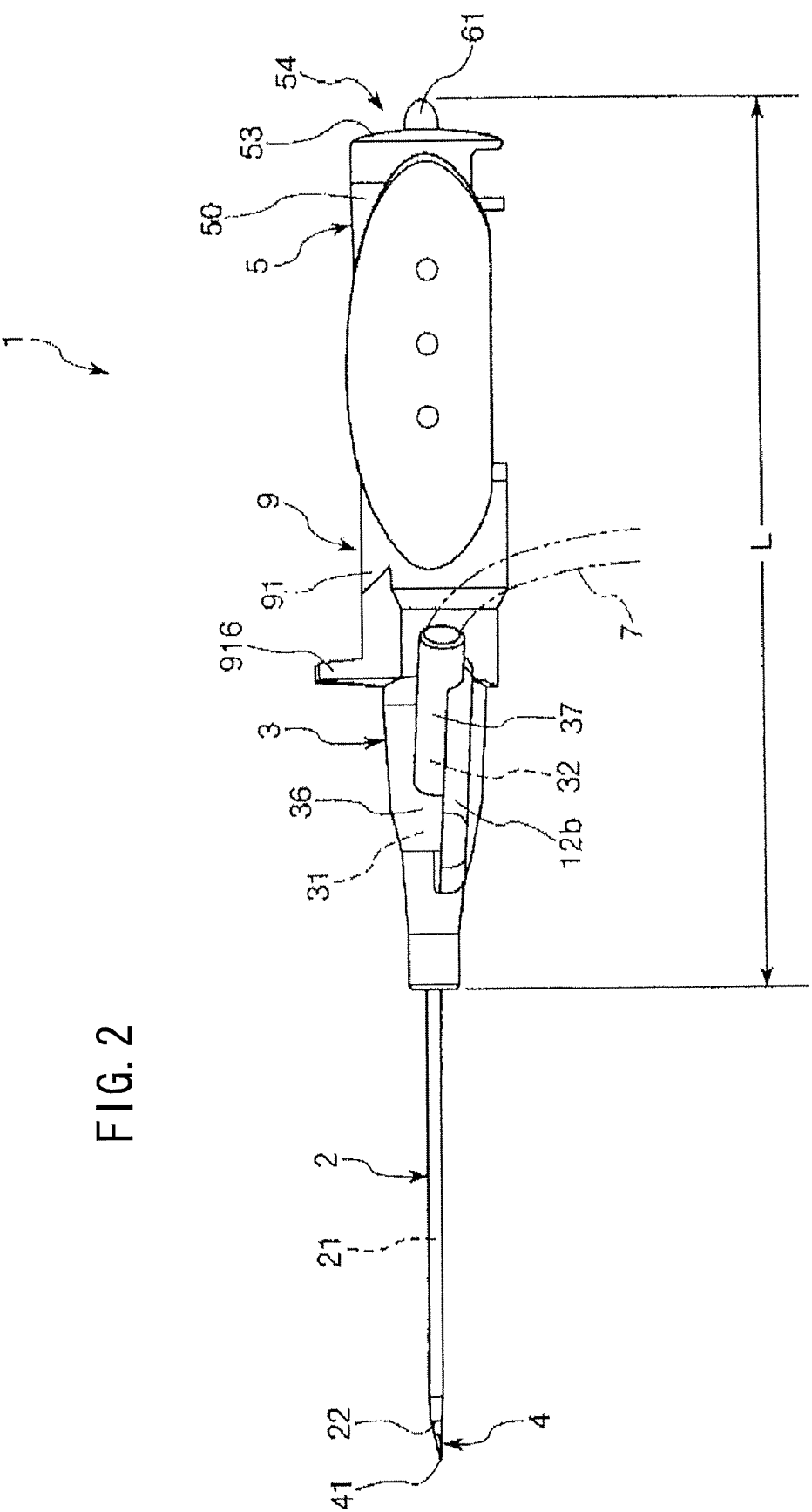
FIG. 2 is a side view of the indwelling needle assembly shown in FIG. 1.
Figure 3:
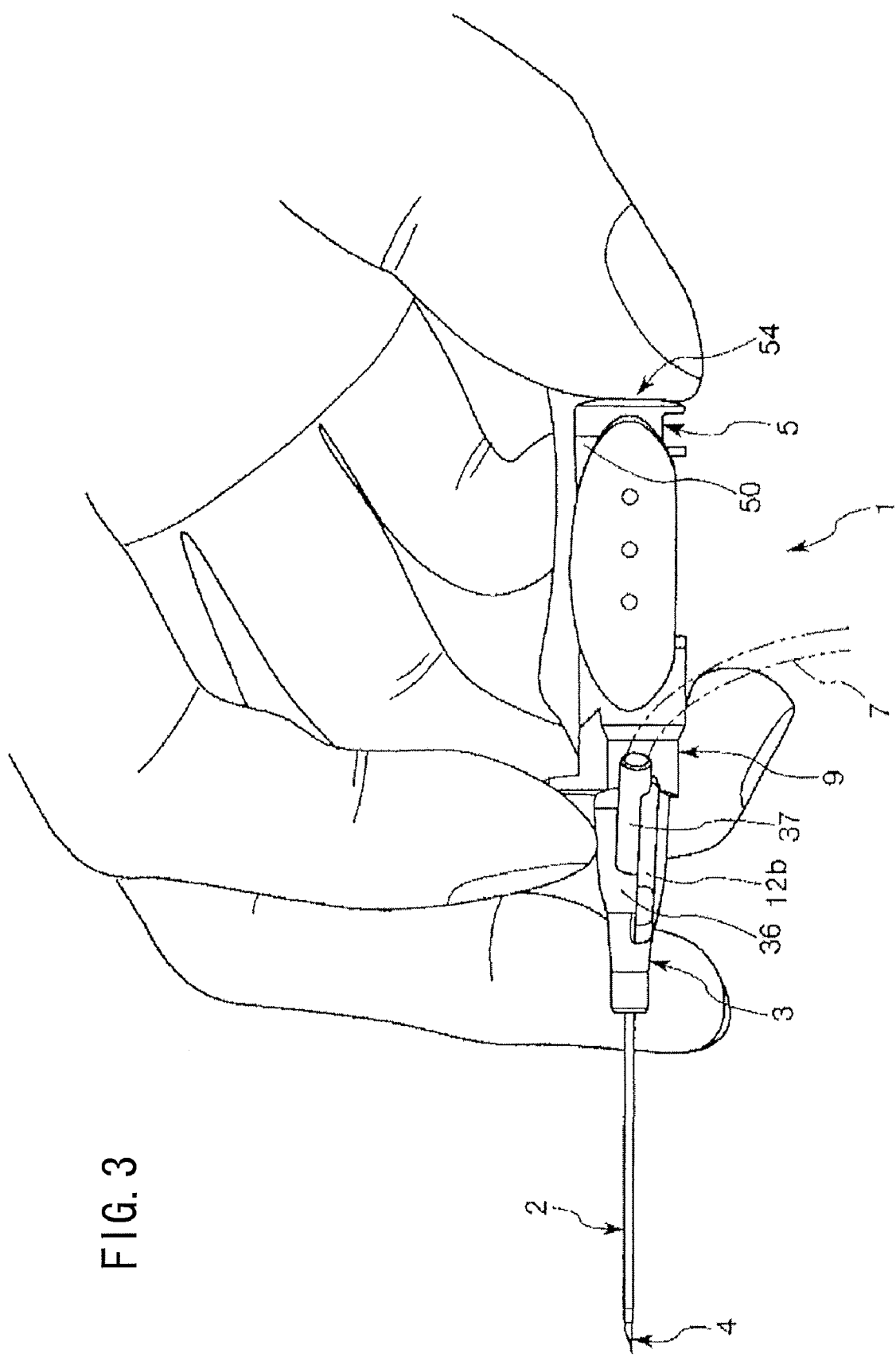
FIG. 3 is a side view showing a condition where the indwelling needle assembly shown in FIG. 1 is held.
Figure 4:
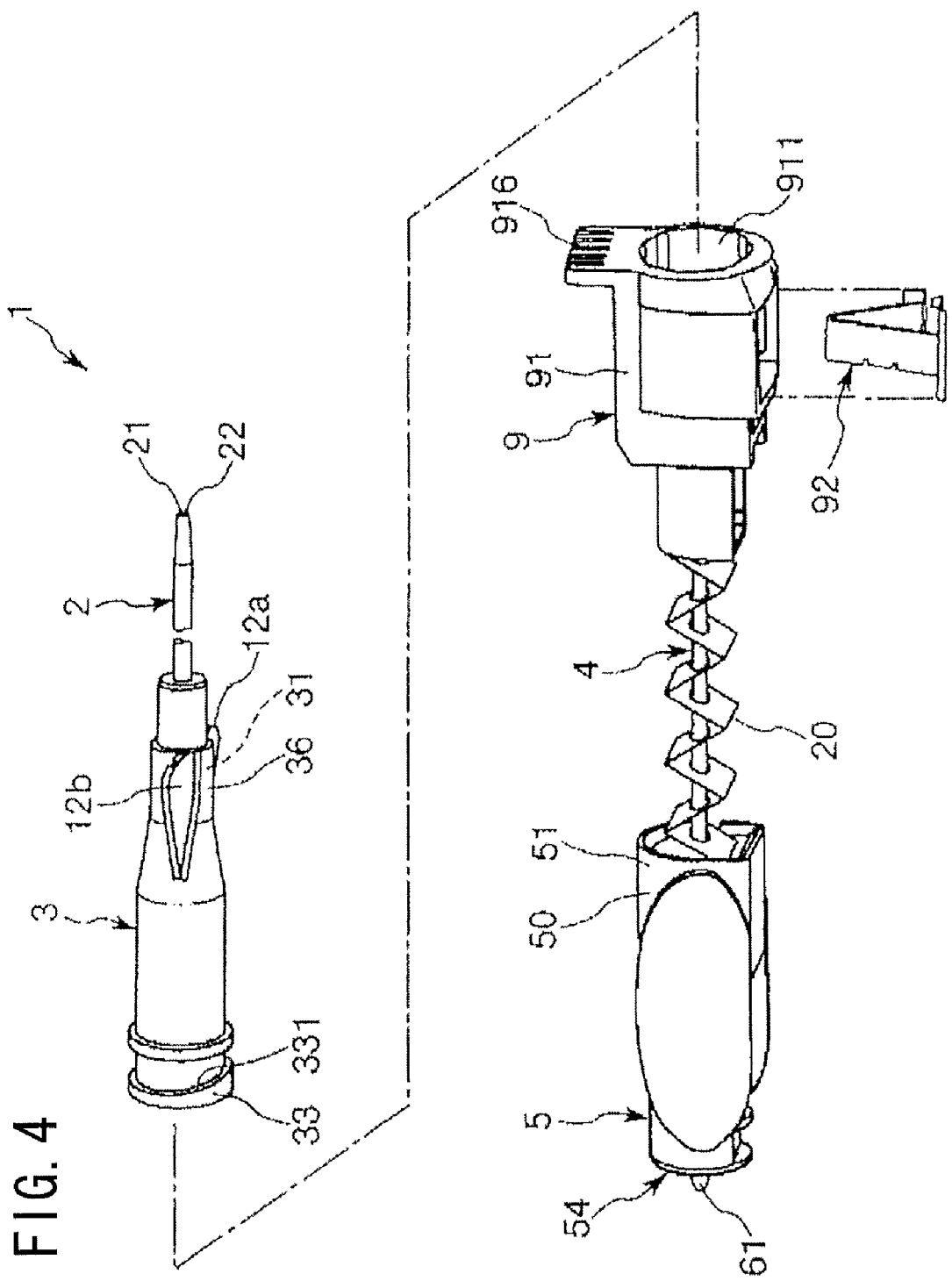
FIG. 4 is an exploded perspective view of the indwelling needle assembly shown in FIG. 1.
Figure 5:
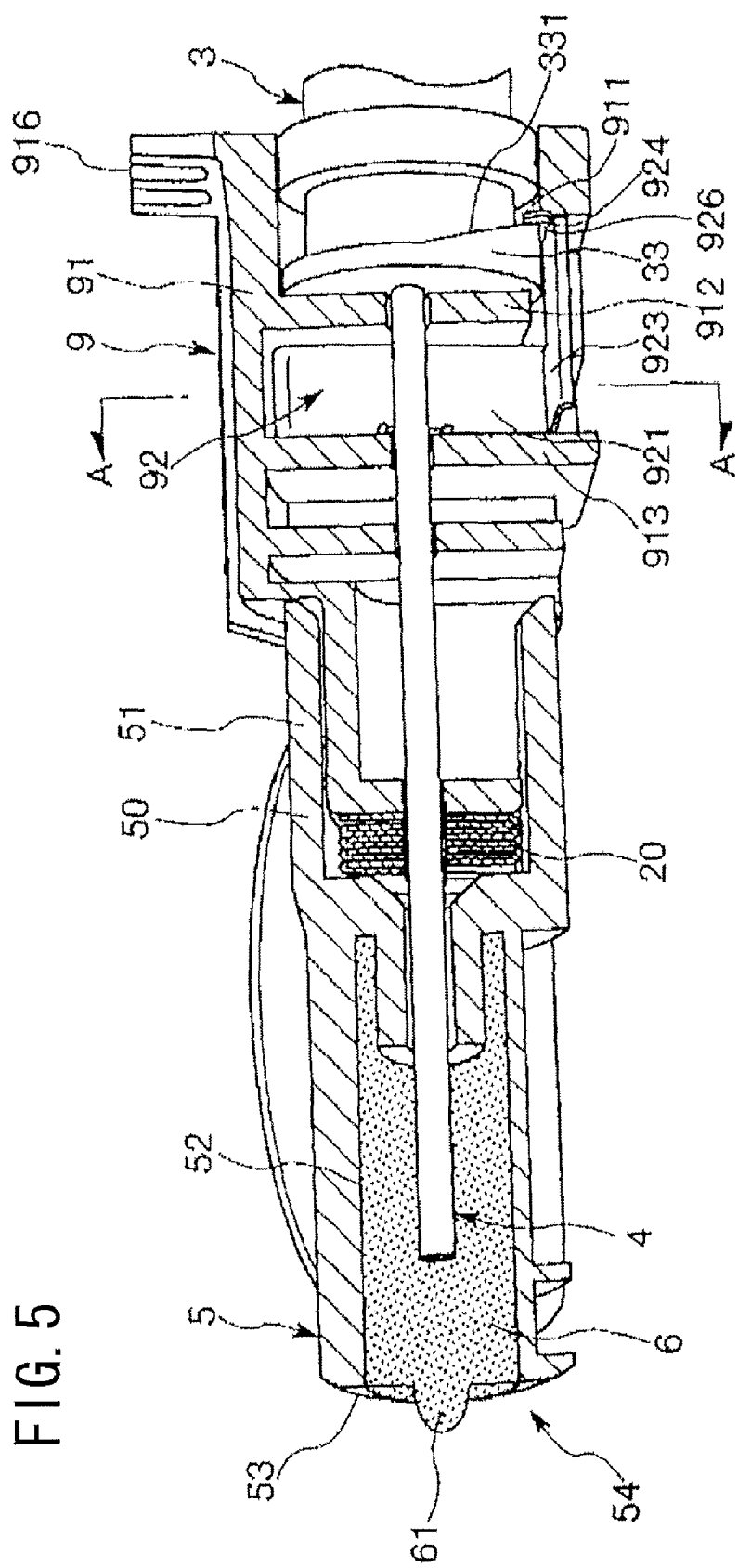
FIG. 5 is a sectional view showing an outer needle hub, an inner needle, an inner needle hub, a protector, etc. of the indwelling needle assembly shown in FIG. 1.
Figure 6:
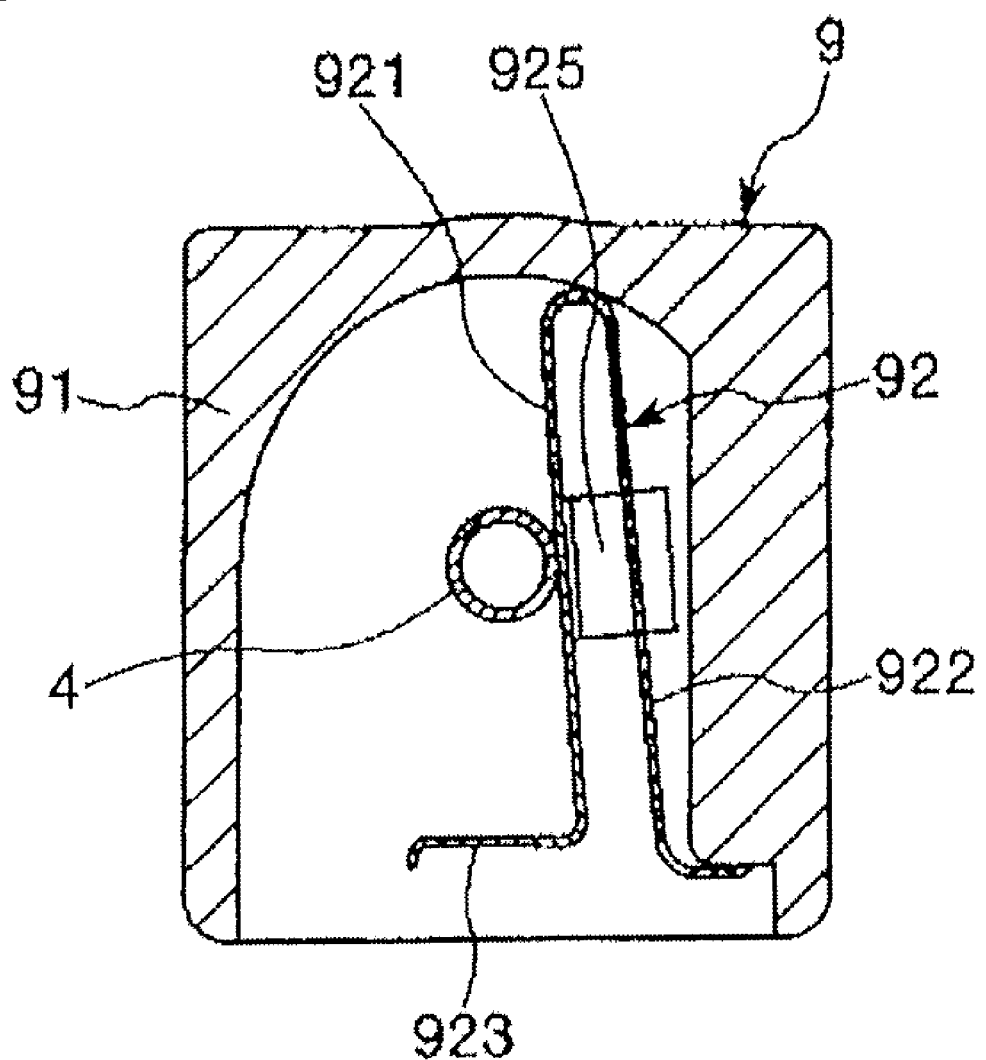
FIG. 6 is a sectional view taken along line A-A of FIG. 5.
Figure 7:
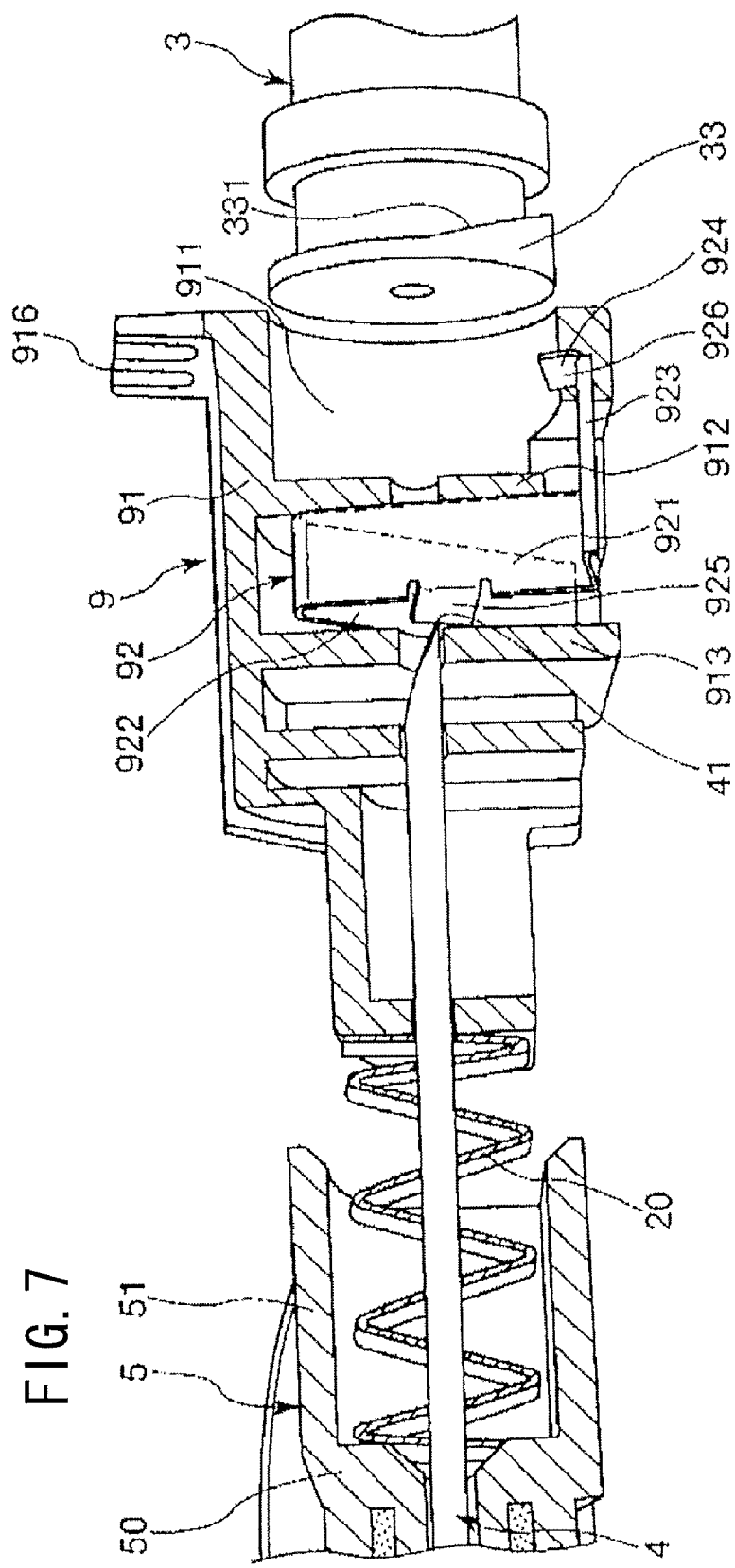
FIG. 7 is a sectional view showing the outer needle hub, the inner needle, the inner needle hub, the protector, etc. of the indwelling needle assembly shown in FIG. 1.
Figure 8:
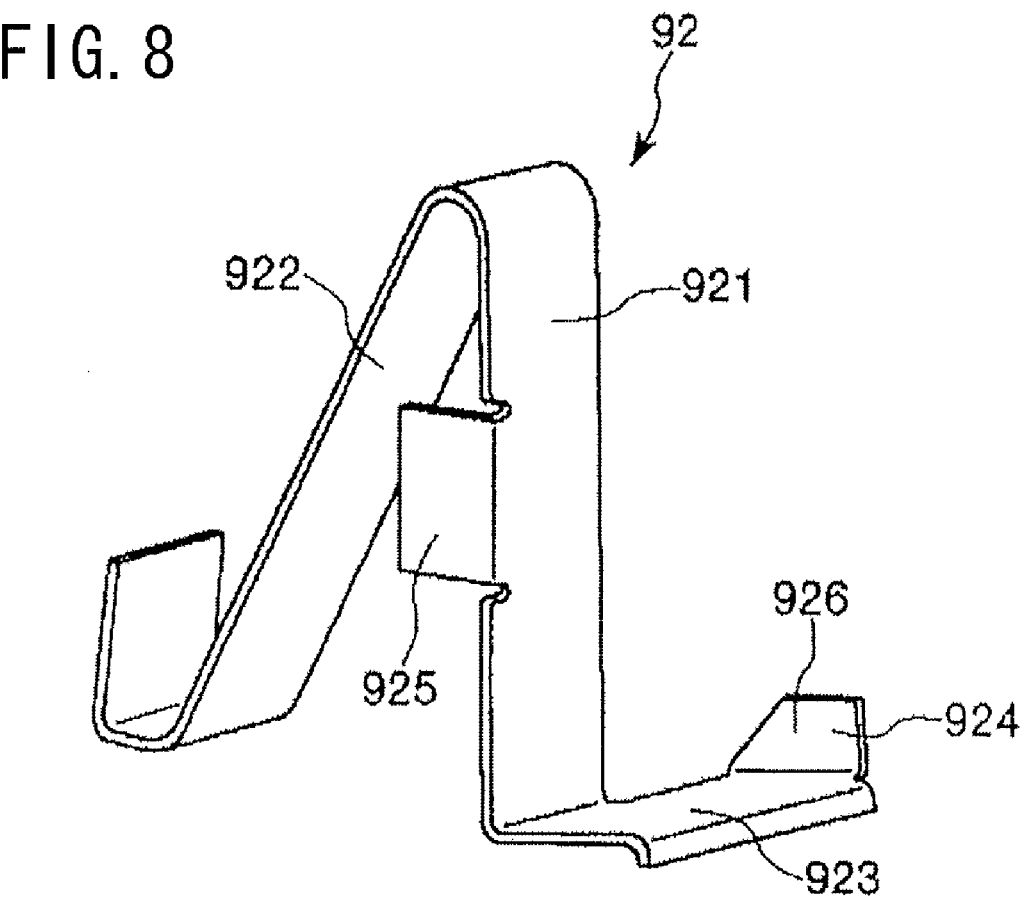
FIG. 8 is a perspective view showing a coupling member of the protector in the indwelling needle assembly shown in FIG. 1.

FIG. 1 is a perspective view showing a first embodiment of the indwelling needle assembly according to an embodiment of the present invention; FIG. 2 is a side view of the indwelling needle assembly shown in FIG. 1; FIG. 3 is a side view showing a condition where the indwelling needle assembly shown in FIG. 1 is held; FIG. 4 is an exploded perspective view of the indwelling needle assembly shown in FIG. 1; FIG. 5 is a sectional view showing an outer needle hub, an inner needle, an inner needle hub, a protector, etc. of the indwelling needle assembly shown in FIG. 1; FIG. 6 is a sectional view taken along line A-A of FIG. 5; FIG. 7 is a sectional view showing the outer needle hub, the inner needle, the inner needle hub, the protector, etc. of the indwelling needle assembly shown in FIG. 1; FIG. 8 is a perspective view showing a coupling member of the protector in the indwelling needle assembly shown in FIG. 1; and FIGS. 9 and 10 each are bottom views showing schematically the outer needle hub and the coupling member of the protector in the indwelling needle assembly shown in FIG. 1.

Incidentally, in the following description, the right side in FIGS. 2, 3, 9 and 10 will be taken as "proximal (trailing end)" and the left side as "distal (leading end)." In addition, the left side in FIGS. 4, 5 and 7 will be taken as "proximal (trailing end)" and the right side as "distal (leading end)." Further, in FIGS. 9 and 10, of a coupling member of a protector, only a first part and a projection piece are drawn.

An indwelling needle assembly 1 shown in the drawings has a hollow outer needle 2, an outer needle hub 3 fixed to a proximal portion of the outer needle 2, an inner needle 4 to be inserted into the outer needle 2, an inner needle hub 5 which is fixed to a proximal portion of the inner needle 4 and which is provided with a finger hold 54 at its proximal portion to be contacted by the thumb of a hand holding the indwelling needle assembly 1, and a tube 7 which is connected to a side portion of the outer needle hub 3 so that its lumen 71 communicates with a lumen 21 of the outer needle 2. Incidentally, while this indwelling needle assembly 1 is to be used, particularly, in the state of being held by fingers of a hand wearing a medical glove (hereinafter referred also to simply as "glove"), but, naturally, it may be used in the state of being held by fingers of an ungloved hand.

The outer needle 2, preferably, has a certain degree of flexibility. The material constituting the outer needle 2 is preferably a resin material, particularly, a soft or flexible resin material. Specific examples of the material include fluororesins such as PTFE, ETFE, PFA, etc., olefin resins such as polyethylene, polypropylene, etc. and mixtures thereof, polyurethane, polyesters, polyamides, polyether nylon resins, mixtures of an olefin resin with an ethylene-vinyl acetate copolymer, etc.

A portion or the entirety of the outer needle 2 as above may enable the inside thereof to be visible. In addition, the outer needle 2 may be provided with radiopacity by blending a radiopaque material such as barium sulfate, barium carbonate, bismuth carbonate, tungstic acid, etc. into the material constituting the outer needle 2.

The outer needle hub 3 is fixed, in a liquid-tight fashion, to a proximal portion of the outer needle 2 by, for example, caulking, fusing (heat fusing, microwave fusing, etc.), adhesion with an adhesive, or the like.

The outer needle hub 3 has a main pipe 36 which is substantially tubular, and a side pipe 37 which is substantially tubular and which has a branch flow path 32 branched from a flow path 31 in the main pipe 36.

As above-mentioned, a proximal portion of the outer needle 2 is fixed to the distal side of the main pipe 36, and the flow path 31 communicates with the lumen 21 of the outer needle 2 on the distal side thereof. The flow path 31 is so disposed that its axis coincides substantially with the center axis of the outer needle 2.

On the other hand, the branch flow path 32 (side pipe 37) is so disposed that its axis is inclined at a predetermined angle in relation to the center axis of the outer needle 2, that is, the axis of the flow path 31. In this case, the branch flow path 32 is so inclined that the proximal side of the branch flow path 32 is located on the right side in FIGS. 1 to 3. Incidentally, the axis of the branch flow path 32 may be perpendicular to the axis of the flow path 31.

Further, a distal portion of the tube 7 is connected to the side pipe 37 of the outer needle hub 3. This ensures that a liquid such as a medicinal liquid can be supplied into the outer needle 2 through the tube 7.

In addition, the outer needle hub 3 is formed with a rib 33 at a proximal portion thereof. The rib 33 will be described in detail later.

Further, on lateral sides of the outer needle hub 3, a pair of wings 12a and 12b are formed integrally with the outer needle hub 3. At the time of puncturing a blood vessel or the like with the outer needle 2 and the inner needle 4, puncturing is conducted by holding the indwelling needle assembly 1, and, when the distal end of the outer needle 2 has entered the blood vessel, the outer needle hub 3 is advanced while pushing a finger hold 916 (described later) by an index finger, whereby only the outer needle 2 can be advanced into the inside of the blood vessel. At the time of leaving the outer needle 2 indwelling, the wings 12a and 12b are fixed to a skin by a pressure sensitive adhesive tape or the like.

The inner needle 4 having a sharp needle point 41 at the distal end thereof is inserted into the outer needle 2. The indwelling needle assembly 1 is used in a condition where the inner needle 4 is inserted into the outer needle 2 and the needle point 41 protrudes from a tip opening (distal end) 22 of the outer needle 2, that is, in the condition shown in FIGS. 1 to 3, 5, 6 and 9. Hereinafter, this condition will be referred to as the "assembled condition."

The length of the inner needle 4 is set to such a value that at least the needle point 41 protrudes from the tip opening 22 of the outer needle 2 in the assembled condition.

The inner needle 4 may be a hollow needle, or may be a solid (non-hollow) needle.

In the configuration shown in the drawings, the inner needle 4 is a hollow needle, which is formed with a hole (side hole) (not shown) in a side portion of an intermediate part thereof. This ensures that when a blood vessel is punctured with the inner needle 4, blood flows into the hollow portion of the inner needle 4, and the blood, in its course of flowing, flows through the hole formed in the side portion of the inner needle 4 into a gap between the inner needle 4 and the outer needle 2, which permits flashback of the blood to be confirmed earlier.

Incidentally, the inner needle 4 may have a configuration including both a hollow portion and a solid portion (for example, a configuration obtained by filling up a part of the lumen of a hollow needle so that the needle is hollow on the distal side and solid on the proximal side). Where the inner needle is wholly composed of a single member, a reduction in the cost of the inner needle 4 can be promised.

In addition, the inner needle 4 may be uniform in outside diameter, or may have a plurality of portions which are different in outside diameter.

Examples of the material constituting the inner needle 4 include metallic materials such as stainless steel, aluminum, aluminum alloys, titanium, titanium alloys, etc.

As shown in FIG. 5, the inner needle hub 5 is adhered (fixed) to a proximal portion of the inner needle 4 with an adhesive 6. Specifically, the inner needle hub 5 has an inner needle hub body part 50, and the proximal portion of the inner needle 4 is adhered and fixed to the inner needle hub body part 50 with the adhesive 6.

To be more specific, the inner needle hub body part 50 has a recess 52 opening at the proximal end thereof. A proximal portion of the inner needle 4 is disposed inside the recess 52, and the recess 52 is filled with the adhesive 6, whereby the inner needle 4 is adhered and fixed to the inner needle hub body part 50 with the adhesive 6 at the proximal portion thereof. In the configuration shown in the figure, the inner needle 4 is hollow, and, therefore, the inner needle 4 can be sealed with the adhesive 6 so that the blood flowing back upon puncturing of a blood vessel is prevented from flowing out from a proximal portion of the inner needle hub 5.

In addition, the inner needle hub body part 50 is provided with a protector insertion part (a connecting member accommodation part) 51 at a distal portion thereof into which a proximal portion of a protector 9 (described later) is inserted and a connecting member 20 (described later) is accommodated in the assembled condition. The protector 9 and the connecting member 20 can be moved relative to the protector insertion part 51.

Incidentally, the finger hold 54 will be detailed later.

Each of the inner needle hub 5 as above and the outer needle hub 3 as above-described is preferably formed of a transparent (colorless transparent) or colored transparent or semi-transparent resin, so as to ensure visibility of the inside thereof. This ensures that when the outer needle 2 is securely inserted into a blood vessel, the flashback of the blood flowing in through the aforementioned inner needle 4 can be confirmed visually.

Materials constituting the outer needle hub 3, the inner needle hub 5 and the wings 12a and 12b are not particularly limited. Examples of the respective materials constituting the outer needle hub 3 and the wings 12a, 12b include various resin materials, for example, polyolefins such as polyethylene, polypropylene, an ethylene-vinyl acetate copolymer, etc., polyurethane, polyamides, polyesters, polycarbonate, polybutadiene, polyvinyl chloride, polyacetal, etc. The material constituting the inner needle hub 5 will be described later.

The tube 7 is flexible, and its distal portion is connected to the side pipe 37 of the outer needle hub 3, as mentioned above. The tube 7 is provided with a branching part at its proximal portion where the flow path is branched into two branch flow paths, one of which is fitted with a connector 72 and the other of which is fitted with a connector 73. Each of the connectors 72 and 73 is connected to, for example, a connector equipped at an end portion of an infusion line for supplying an infusion liquid (medicinal liquid) to be administered, a mouth part of a syringe filled with a medicinal liquid, or the like.

Incidentally, the material constituting the tube 7 is not particularly limited. Examples of the material include polyolefins such as polyethylene, polypropylene, an ethylene-vinyl acetate copolymer, etc., polyvinyl chloride, polybutadiene, polyamides, polyurethane, polyesters, etc.

In addition, the indwelling needle assembly 1 is provided, in the flow path 31 in the outer needle hub 3, with a cylindrical (block-formed) seal member (not shown) as sealing means for sealing the flow path 31. The seal member is disposed on the proximal side, relative to the branch flow path 32, of the flow path 31 in the main pipe 36. In this embodiment, the seal member is arranged in the vicinity of the branch flow path 32.

The seal member is formed with a hole or slit which permits the inner needle 4 to be inserted thereinto and therethrough and which is closed when the inner needle 4 thus inserted is pulled out. In this embodiment, the seal member is formed substantially in its center with a slit (not shown) which penetrates the seal member in the longitudinal direction of the seal member.

The slit is in the shape of a straight line segment. This ensures that the slit in a closed state can easily be put into an open state. Therefore, the inner needle 4 can be smoothly passed through the seal member (slit). Specifically, when the outer needle 2 is advanced using the inner needle 4 as a guide, which will be described later, the frictional resistance between the outer surface of the inner needle 4 and the inner surface of the slit can be reduced. Accordingly, operability at the time of a puncturing operation of the indwelling needle assembly 1 is further enhanced.

The seal member has a self-closing property such that the inner needle 4 is inserted into and through the slit in the assembled condition and that, when the inner needle 4 thus inserted is pulled out, the slit is closed by an elastic force (restoring force) possessed by the seal member itself. This ensures that when the inner needle 4 is pulled out, leakage of liquid from the proximal end of the outer needle hub 3 can be prevented from occurring and that the inside of the outer needle hub 3 can be maintained in an aseptic condition.

Examples of the material constituting the seal member as above include various elastic materials such as various rubber materials (particularly, vulcanized ones) such as natural rubber, isoprene rubber, butyl rubber, butadiene rubber, styrene-butadiene rubber, urethane rubber, nitrile rubber, acrylic rubber, fluoro-rubber, silicone rubber, etc., various thermoplastic elastomers based on urethane, polyester, polyamide, olefin, styrene or the like, and mixtures of them.

In addition, the indwelling needle assembly 1, preferably, is preliminarily subjected to a friction-reducing treatment for reducing the frictional resistance between the inner surface of the slit and the outer surface of the inner needle 4.

Examples of the friction-reducing treatment include a treatment in which a lubricant is applied to at least one of the inner surface of the slit and the outer surface (outer peripheral surface) of the inner needle 4, and a treatment in which a layer formed of a low-friction material (low-friction layer) is formed on the inner surface of the slit.

Such a friction-reducing treatment ensures that when the outer needle 2 is advanced using the inner needle 4 as a guide, the frictional resistance between the inner needle 4 and the seal member can be reduced assuredly. Consequently, the outer needle 2 can be moved smoothly, and the indwelling needle assembly 1 is made to be excellent in operability at the time of a puncturing operation.

In addition, the indwelling needle assembly 1 has the protector 9 which covers at least the needle point 41 of the inner needle 4 when the inner needle 4 is drawn out of the outer needle 2. The description of the protector 9 will be made in the following.

In the assembled condition, the protector 9 is inserted into the protector insertion part 51 of the inner needle hub 5.

The protector 9 is detachably coupled to the outer needle hub 3. As shown in FIGS. 4, 5 and 7, the protector 9 has a protector body 91 and a coupling member 92 provided inside the protector body 91.

The protector body 91 is provided with a bottomed hole part 911 at its distal portion, into which a proximal portion of the outer needle hub 3 is inserted in the assembled condition.

The material constituting the protector body 91 is not particularly limited. For example, materials identical or similar to those mentioned above as material for constituting the outer needle hub 3 and the inner needle hub 5 can be used.

Besides, the coupling member 92 is accommodated on the proximal side in the hole part 911 of the protector body 91. Specifically, the protector body 91 is provided with a wall part 912 which constitutes a bottom wall of the hole part 911, and a wall part 913 which is disposed on the proximal side of the wall part 912, and the coupling member 92 is disposed between the wall part 912 and the wall part 913.

As shown in FIGS. 5, 7 and 8, the coupling member 92 has a plate-like projection piece 924 which is elastic and capable of engagement with the rib 33 of the outer needle hub 3. In the assembled condition, the protector 9 is detachably coupled to the outer needle hub 3 through the engagement between the projection piece 924 of the coupling member 92 and the rib 33 of the outer needle hub 3, in the condition where a proximal portion of the outer needle hub 3 is inserted into the hole part 911 of the protector 9.

In this embodiment, the coupling member 92 is substantially V-shaped as a whole, and is a member (plate spring) formed by bending an elastic belt-like plate member into a substantially V-shaped form. Specifically, the coupling member 92 includes a first part 921, a second part 922 which is connected to the upper side in FIG. 8 of the first part 921 and which forms the substantially V-shaped form together with the first part 921, a third part 923 disposed on the lower side in FIG. 8 of the first part 921, the projection piece 924 projecting toward the upper side in FIG. 8 from the proximal end of the third part 923, and a shutter part 925 arranged on the proximal side at an intermediate portion of the first part 921. In addition, a part on the lower side in FIG. 8 of the second part 922 is curved or bent toward the upper side. Besides, an opposed surface 926, opposed to a sliding surface 331 of the rib 33 (described later), of the projection piece 924 is substantially perpendicular to the center axis $O_1$ of the inner needle 4.

The coupling member 92 can assume a first state in which its projection piece 924 is in engagement with the rib 33 and a second state in which the projection piece 924 is out of engagement with the rib 33, through a change in the opening angle between the first part 921 and the second part 922.

Figure 9:
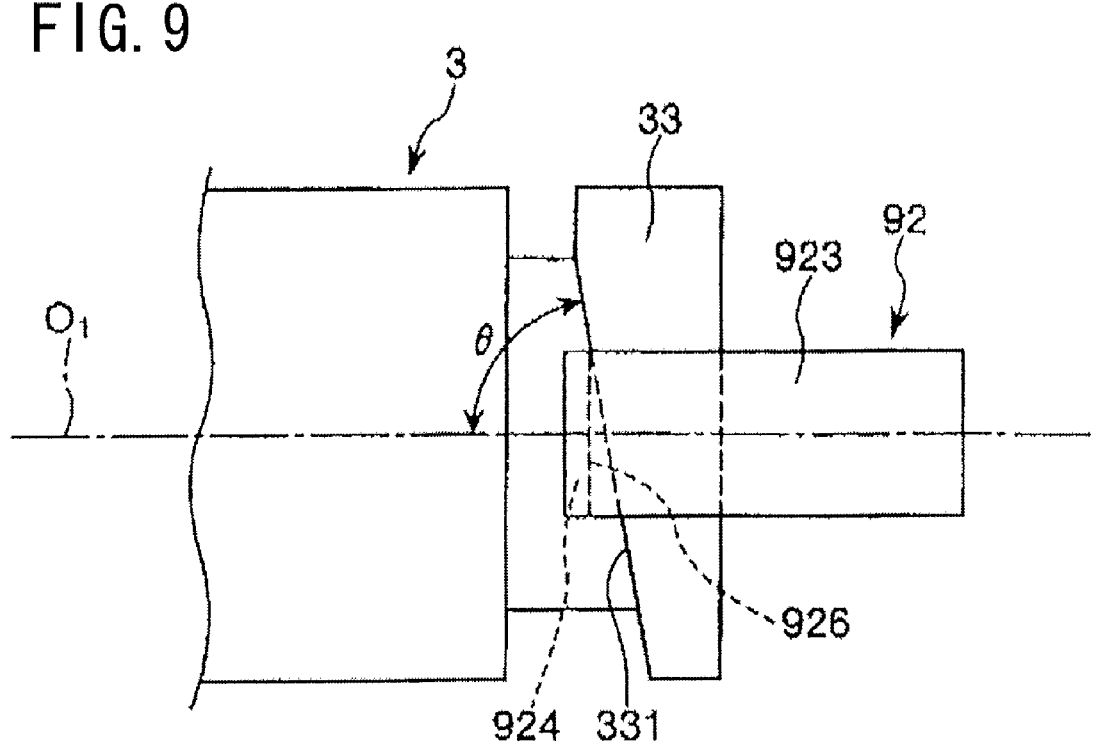
FIG. 9 is a bottom view showing schematically the outer needle hub and the coupling member of the protector in the indwelling needle assembly shown in FIG. 1.

To be more specific, in the assembled condition as shown in FIGS. 5, 6 and 9, the coupling member 92 is accommodated in the state of being folded to have a small opening angle, with its first part 921 in contact with the outer peripheral surface of the inner needle 4, whereby the coupling member 92 is maintained in the first state. In this state, the protector 9 is coupled with the outer needle hub 3. Besides, the protector 9 and the outer needle hub 3 can be moved, in the longitudinal direction of the inner needle 4, relative to the inner needle 4 and the inner needle hub 5.

Figure 10:
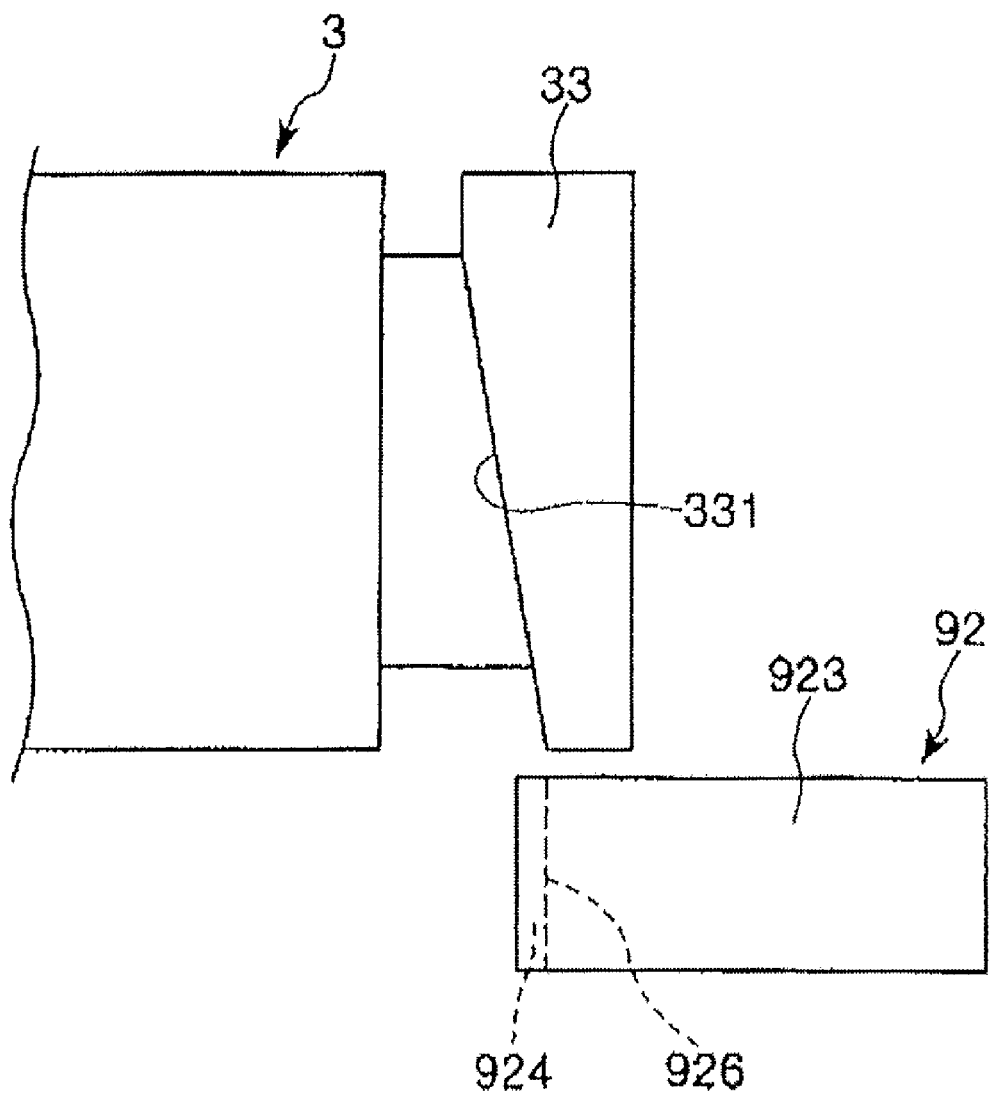
FIG. 10 is a bottom view showing schematically the outer needle hub and the coupling member of the protector in the indwelling needle assembly shown in FIG. 1.

When, starting from this condition, the inner needle hub 5 is moved in the proximal direction relative to the protector 9 and the needle point 41 of the inner needle 4 reaches the proximal side of the first part 921 of the coupling member 92, the coupling member 92 opens under its own elastic force as shown in FIGS. 7 and 10 and is pulled in the proximal direction through the connecting member 20 (described later), resulting in the second state. The direction in which the projection piece 924 is moved by the restoration of the coupling member 92 is substantially perpendicular to the center axis $O_1$ of the inner needle 4. In this condition, the protector 9 and the outer needle hub 3 are out of mutual coupling. In addition, the shutter part 925 of the coupling member 92 is located on the distal side of the needle point 41 on the center axis $O_1$ of the inner needle 4, whereby the needle point 41 is inhibited from moving in the distal direction beyond the coupling member 92. Incidentally, when the inner needle hub 5 is further moved in the proximal direction, the protector 9 is pulled and moved in the proximal direction through the connecting member 20 (described later), thereby being disengaged from the outer needle hub 3.

The material constituting the coupling member 92 is not particularly limited. Examples of the material include various resin materials identical or similar to those mentioned above as material for the outer needle hub 3 and the inner needle hub 5, and various metallic materials such as stainless steel, aluminum, aluminum alloys, titanium, titanium alloys, copper, copper alloys, etc.

Part of the coupling member 92 may be fixed to the protector body 91 by, for example, caulking, press fitting, fusing, adhesion with an adhesive, or the like. Besides, the coupling member 92 is not limited to the configuration shown in the drawings but may be of other form or structure.

In addition, at a distal portion of the protector body 91, the finger hold 916 is formed in a projecting form. The protector body 91 and the finger hold 916 are formed integrally with each other. Besides, the finger hold 916 projects toward the upper side. With the finger hold 916 pushed in the distal direction by a finger, the outer needle 2 can be moved in the distal direction relative to the inner needle 4.

Incidentally, the protector body 91 and the finger hold 916 may be formed as separate members and may be joined to each other. In this case, the material constituting the finger hold 916 is not particularly limited; for example, materials identical or similar to those mentioned above as material for constituting the outer needle hub 3 can be used. In addition, the finger hold 916 may be projectingly formed on other part, for example, the outer needle hub 3.

Besides, as shown in FIGS. 4, 5 and 7, the indwelling needle assembly 1 has the connecting member 20 which has both a slip-off preventing function for preventing the protector 9 from slipping off the needle point 41 of the inner needle 4 when the needle point 41 has been covered by the protector 9, and a connecting function for connecting the protector 9 and the inner needle hub 5 to each other.

The connecting member 20 is so configured as to interconnect the protector body 91 of the protector 9 and the inner needle hub 5. This ensures that when the inner needle hub 5 is moved in the proximal direction, the protector 9 is pulled in the proximal direction through the connecting member 20.

In addition, the connecting member 20 is bellows-like in form and, hence, can be contracted and extended. The connecting member 20 has such a length that, when the connecting member 20 is in its maximally extended state (a fully extended state), the needle point 41 of the inner needle 4 is located on the proximal side relative to the shutter part 925 of the coupling member 92 and the needle point 41 is accommodated in the protector body 91 (the needle point 41 would not slip off from the protector body 91).

Thus, the connecting member 20 connects the protector body 91 and the inner needle hub 5 to each other and has such a length that, when the connecting member 20 is in its maximally extended state, the needle point 41 is accommodated in the protector body 91. Therefore, the protector 9 is securely prevented from slipping off from the needle point 41 of the inner needle 4, and, accordingly, the condition where the needle point 41 is covered by the protector 9 can be maintained assuredly. Consequently, an accident is securely prevented, in which the worker or the like sticks the needle point 41 in his or her finger or the like by mistake at the time of discarding the inner needle 4 or in other similar situations, so that high safety is attained.

In addition, the connecting member 20 is contracted, or folded, in the assembled condition, and is extended, or unfolded, in the condition where the inner needle 4 has been pulled out of the outer needle 2 and the needle point 41 is covered by the protector 9.

Such a connecting member 20 is contracted in the assembled condition, and is accommodated, in the contracted state, in the protector insertion part 51 of the inner needle hub 5, on the proximal side relative to the protector 9. This ensures that at the time of a puncturing operation, the connecting member 20 would not obstruct the operation and, therefore, operability of the indwelling needle assembly 1 is enhanced. In addition, there is also obtained a merit of a reduction in the size of the indwelling needle assembly 1.

Besides, when the connecting member 20 is in the contracted state and when it is in the extended state, the inner needle 4 is penetrating the connecting member 20. As a result, the inner needle 4 functions as a guide for the connecting member 20 at the times of contraction and extension of the connecting member 20. Therefore, for example when the indwelling needle assembly 1 is put into the assembled condition (is manufactured), it is possible to securely prevent the connecting member 20 from being contracted in an unwilling state, or from being contracted without being accommodated in the inner needle hub 5.

In addition, the connecting member 20 has a self-restoring property with which it tends to return to its natural state. Therefore, in the state of being contracted more than in its natural state, the connecting member 20 functions as biasing means for biasing in the extending direction by its restoring force; in the state of being extended more than in its natural state, the connecting member 20 functions as biasing means for biasing in the contracting direction by its restoring force. The term "natural state" used herein means the condition where no external force is acting on the connecting member 20.

The connecting member 20 may be so configured as to connect the protector 9 and the inner needle 4 to each other.

As shown in FIGS. 4, 5, 7, 9 and 10, the outer needle hub 3 of the indwelling needle assembly 1 is provided with the rib 33 at a proximal portion thereof as a projected part capable of engagement with the projection piece 924 of the coupling member 92 of the protector 9 described above.

The rib 33 is formed on the outer peripheral surface of a proximal portion of the outer needle hub 3 along the circumferential direction. In the configuration shown in the drawings, the rib 33 is annular in shape.

The rib 33 has the sliding surface 331 which is inclined in relation to the center axis (axis) $O_1$ of the inner needle 4 and on which the projection piece 924 slides. In this configuration, when the coupling member 92 is shifted from the first state shown in FIGS. 5, 6 and 9 to the second state shown in FIGS. 7 and 10, the projection piece 924 of the coupling member 92 slides along the sliding surface 331. Specifically, when the inner needle 4 is pulled out of the outer needle 2, the coupling member 92 is restored as its first part 921 is separated from the outer peripheral surface of the inner needle 4, and, when the coupling member 92 is thus restored, the projection piece 924 slides along the sliding surface 331 of the rib 33, and the coupling member 92 comes into the second state.

This ensures that, at the time of pulling the inner needle 4 out of the outer needle 2 and releasing the protector 9 from the outer needle hub 3, friction can be reduced. Consequently, the operating of pulling the inner needle 4 out of the outer needle 2 and disengaging the protector 9 from the outer needle hub 3 can be carried out smoothly and assuredly.

In addition, since the sliding surface 331 is inclined, the area of a contact portion between the projection piece 924 and the sliding surface 331 of the rib 33 is small, which ensures that the sliding resistance between the projection piece 924 and the sliding surface 331 of the rib 33 is small. Consequently, the projection piece 924 can be slid along the sliding surface 331 of the rib 33 more smoothly.

The inclination angle $\theta$ of the sliding surface 331 of the rib 33 against the center axis $O_1$ of the inner needle 4 (the angle between the sliding surface 331 and the center axis $O_1$) is less than 90°, and is preferably about 30° to 85°, more preferably about 45° to 80°.

This permits the protector 9 to be released from the outer needle hub 3 more smoothly.

Here, in the process of moving the inner needle hub 5 in the proximal direction relative to the protector 9 starting from the assembled condition and thereby pulling the inner needle 4 out of the outer needle 2, it is preferable to set the inclination angle $\theta$ so as to satisfy the following condition, let the force required in the first state of the coupling member 92 be F1, and let the force required during the period from the moment of movement of the needle point 41 of the inner needle 4 to the proximal side of the coupling member 92 until the projection piece 924 and the rib 33 are disengaged from each other, that is, during the shift of the coupling member 92 from the first state to the second state, be F2.

The condition to be satisfied lies in that F2 is preferably not more than 2×F1, more preferably not more than 1.5×F1, and further preferably not more than F1.

Particularly, it is preferable to set the inclination angle $\theta$ so that F2 and F1 will be approximately equal.

This permits the projector 9 to be released from the outer needle hub 3 more smoothly.

Most part of the force F1 is a force against the frictional resistance between the outer peripheral surface of the inner needle 4 and the first part 921 of the coupling member 92. Besides, most part of the force F2 is a force against the frictional resistance between the projection piece 924 of the coupling member 92 and the sliding surface 331 of the rib 33.

In addition, while the height of the rib 33 is uniform in this embodiment, the height may gradually decrease along the moving direction in the sliding of the projection piece 924 on the sliding surface 331 of the rib 33. Where the height of the rib 33 is thus gradually decreased, the coupling member 92 can be brought into the second state more smoothly and assuredly.

It is preferable that either one or both of the sliding surface 331 of the rib 33 of the outer needle hub 3 and the opposed surface 926 of the projection piece 924 of the coupling member 92 are coated with a lubricant such as a silicone oil, a surfactant, etc. This results in that the sliding resistance between the projection piece 924 and the sliding surface 331 of the rib 33 is reduced, whereby the projection piece 924 of the coupling member 92 can slide along the sliding surface 331 of the rib 33 more smoothly.

In addition, that a portion of the first part 921 of the coupling member 92 which makes contact with the outer peripheral surface of the inner needle 4 is also preferably coated with a lubricant. This reduces the frictional resistance between the outer peripheral surface of the inner needle 4 and the first part 921, ensuring that the inner needle 4 can be moved relative to the protector 9 more smoothly.

Meanwhile, as shown in FIGS. 2 and 5, in the indwelling needle assembly 1, the inner needle hub 5 is provided with a projected part 61 formed by projecting the adhesive 6 to the proximal side relative to a proximal end face 53 of the inner needle hub body part 50. The proximal end face 53 and the projected part 61 constitute the finger hold 54 to be contacted by the thumb of a hand holding the indwelling needle assembly 1.

Here, at the time of setting the outer needle 2 of the indwelling needle assembly 1 indwelling in a patient, a clinician (user) wears gloves, holds the indwelling needle assembly 1 in the assembled condition with his or her fingers, and thereby performs a puncturing operation of puncturing the patient's blood vessel or the like with the outer needle 2 and the inner needle 4. Besides, at the time of this puncturing operation, the clinician may hold the indwelling needle assembly 1 by a method as shown in FIG. 3, for example.

This holding method of manner is herein referred to as "wing port holding," in which the thumb is put in contact with the finger hold 54 (the projected part 61 and the proximal end face 53) provided at the proximal portion of the inner needle hub 5, and one of the remaining fingers (in the configuration shown in the figure, the middle finger) is put in contact with the distal side of the indwelling needle assembly 1, specifically, with the wing 12a of the outer needle hub 3, whereby the indwelling needle assembly 1 is held so as to be pinched in the longitudinal direction thereof. Even in the case of using an indwelling needle assembly which is not provided with the wings 12a, 12b, the above-mentioned wing port holding can be achieved by a method in which, for example, the middle finger is put in contact with the distal side of the indwelling needle assembly, such as the distal end of the outer needle hub, a tapered surface of a distal portion of the outer needle hub, etc.

In the case of holding the indwelling needle assembly 1 by the wing port holding as above, it is possible, by providing the projected part 61, to prevent (or restrain) the thumb from slipping off the finger hold 54 (the proximal end of the inner needle hub 5). As a result, the puncturing operation can be performed easily and safely. Especially, this effect is conspicuous in the case where the indwelling needle assembly 1 is used by holding it with fingers of a gloved hand.

Further, the projected part 61 is protuberant in a central area of the opening of the recess 52. Specifically, the area (projection area) of projection of the projected part 61 onto a plane perpendicular to the center axis $O_1$ of the inner needle 4 is equal to or smaller than the area of projection of the opening of the recess 52 onto the plane. This ensures that the thumb can be more securely prevented from slipping off the proximal end of the inner needle hub 5.

The dimensions of the projected part 61 are not particularly limited but are set appropriately according to various conditions. For instance, the height (the length along the direction of the center axis $O_1$) of the projected part 61 is preferably about 0.1 to 5 mm, more preferably about 0.3 to 2 mm. In addition, the projection area of the projected part 61 is preferably about 0.2 to 20 $mm^2$, more preferably about 0.7 to 13 $mm^2$.

Here, the medical gloves are required to be flexible, fit the hands well, and have strength. Thus, the gloves are preferably formed from such a material as polyvinyl chloride (PVC), natural rubber latex, nitrile rubber, etc. When polyvinyl chloride is used, it is easy to wear the gloves, the gloves would not make hands rough, and the gloves are economical. When natural rubber latex is used, the gloves are excellent in strength and flexibility. When nitrile rubber is used, the gloves are free of allergic problems.

In addition, the inner needle hub body part 50 of the inner needle hub 5 is required to be easy to assemble with the inner needle 4 and other components such as the protector 9, and to have such a degree of transparency that the flashback of blood can be seen therethrough. Besides, the inner needle hub body part 50 is required to be comparatively hard, since it is used also as a holding part.

Examples of the material constituting the inner needle hub body part 50 include various resin materials such as polyolefins such as polyethylene, polypropylene, an ethylene-vinyl acetate copolymer, etc., polyurethane, polyamides, polyesters, polycarbonate, polybutadiene, polyvinyl chloride, polyacetal, etc., among which particularly preferred are polycarbonate, polypropylene and the like. When polycarbonate is used, the inner needle hub body part 50 is excellent in transparency, is hard, can be adhered by use of a solvent, and permits easy assembly. When polypropylene is used, the inner needle hub body part 50 is excellent in chemical resistance, and is good in bio-compatibility.

Further, the adhesive 6 is not particularly limited insofar as it, after cured, is less liable to slip on a glove, specifically, less liable than the inner needle hub body part 50 to slip on the glove. The adhesive 6 is appropriately selected according to various conditions. For example, epoxy adhesives and the like are suitable for forming the projected part 61 therefrom, since they are based on a curing mechanism utilizing a chemical reaction and, hence, are low in shrinkage factor. Further, acrylic adhesives and the like are suitable for forming the projected part 61 therefrom, since they show a high curing rate at normal temperature and, hence, are less liable to dripping or the like at the time of assembly. In addition, for easier formation of the projected part 61, the adhesive is preferably cured in the condition where the indwelling needle assembly 1 is erected perpendicularly to the ground.

Incidentally, the length (distance) L between the distal end of the outer needle hub 3 and the proximal end of the projected part 61 in the indwelling needle assembly 1 in the assembled condition is preferably about 20 to 80 mm, more preferably about 30 to 60 mm. This permits the wing port holding to be achieved easily.

Now, an example of the method of using the indwelling needle assembly 1 will be described in detail below.

It is presumed that the clinician wears medical gloves. It suffices for this step to be performed before the puncturing operation (described later) is conducted.

[1] The indwelling needle assembly 1 is prepared, it is put into the assembled condition (see FIGS. 1, 2, 5, 6 and 9), and a connector equipped at an end portion of an infusion line is preliminarily connected to the connector 72 so that an infusion liquid can be supplied from the infusion line.

Incidentally, in this instance, a predetermined part of the tube 7 or the infusion line is preliminarily pinched, for example, with a clamp (an example of flow path opening/closing means), thereby closing the lumen of the tube 7 or the infusion line.

[2] Next, closure of the tube 7 or the infusion line with the clamp or the like is released, whereby the infusion liquid from the infusion line is introduced through the tube 7 into the outer needle hub 3.

The infusion liquid thus introduced into the outer needle hub 3 fills up the branch flow path 32 and the flow path 31 on the distal side relative to the seal member, and is led into the lumen 21 of the outer needle 2, whereby the lumen 21 of the outer needle 2 is primed with the infusion liquid. In this instance, part of the infusion liquid flows out via the tip opening 22 of the outer needle 2.

[3] When the priming is completed in this manner, the tube 7 or the infusion line is again closed with a clamp or the like provisionally, and the indwelling needle assembly 1 is held by the above-mentioned wing port holding.

[4] Subsequently, the outer needle 2 and the inner needle 4 integrated with each other are made to puncture a patient's blood vessel (living body).

When the outer needle 2 is securely inserted into the blood vessel, the internal pressure in the blood vessel causes blood to flow back in the proximal direction through the inner needle 4 and through the lumen 21 of the outer needle 2, and this blood flow can be confirmed in at least one location, where inside visibility is secured, of the outer needle 2, the outer needle hub 3, the inner needle hub 5 and the tube 7.

After the backward blood flow is confirmed, the outer needle 2 is further advanced by a minute distance in the distal direction along the inner needle 4 and with the inner needle 4 as a guide.

Besides, at the time of puncturing the blood vessel in this manner, the lumen 21 of the outer needle 2 has already been primed with the infusion liquid, so that erroneous penetration of a bubble or bubbles into the blood vessel is securely prevented and, hence, safety is extremely high.

[5] After the outer needle 2 has captured (securely punctured) the blood vessel, the outer needle 2 or the outer needle hub 3 is fixed by one hand, and the inner needle hub 5 is gripped by the other hand and pulled in the proximal direction. By this, a series of operations from withdrawal of the inner needle 4 from the outer needle 2 to the release of the protector 9 from the outer needle hub 3 are carried out sequentially and continuously. Specifically, first, the inner needle 4 is moved in the proximal direction, and is drawn out of the outer needle 2.

[6] When the inner needle 4 is further moved in the proximal direction and the needle point 41 is passed through the inside of the slit, the seal member having the self-closing property closes the slit by its own elastic force. This prevents leakage of liquid through the slit from occurring, and ensures that the sterility in the outer needle hub 3 and the infusion line is secured.

[7] When the inner needle 4 is further moved in the proximal direction and the needle point 41 reaches the proximal side of the first part 921 of the coupling member 92, as shown in FIGS. 7 and 10, the coupling member 92 opens under its own elastic force, and is pulled and moved in the proximal direction through the connecting member 20, to be brought into the second state.

In this case, as above-mentioned, the direction in which the projection piece 924 is moved due to restoration of the coupling member 92 is substantially perpendicular to the center axis $O_1$ of the inner needle 4. In this instance, since the protector 9 is pulled and moved in the proximal direction through the connecting member 20, the coupling member 92 is also moved in the proximal direction attendant on the proximal movement of the protector 9. As a result, the projection piece 924 is slid along the sliding surface 331 of the rib 33, and the coupling member 92 is brought into the second state. When the coupling member 92 is thus brought into the second state, any distal returning movement again of the needle point 41 of the inner needle 4 is impossible, since the needle point 41 is in abutment on the shutter part 925 of the coupling member 92.

[8] Further, the inner needle hub 5 is moved in the proximal direction, whereby the protector 9 is pulled and moved in the proximal direction through the connecting member 20, to be separated (released) from the outer needle hub 3.

Since the connecting member 20 has such a length that the needle point 41 is accommodated in the protector body 91 when the connecting member 20 is in its maximally extended state, the protector 9 can be securely prevented from slipping off from the needle point 41. Accordingly, the condition where the needle point 41 is covered by the protector 9 can be maintained assuredly.

After the inner needle 4 is drawn out of the outer needle 2 in this manner, the inner needle 4 and the inner needle hub 5 are useless and, hence, are put to disposal.

Thus, the inner needle 4 has its needle point 41 covered by the protector 9. Particularly, the possibility that the needle point 41 might move in the distal direction beyond the shutter part 925 of the coupling member 92 to protrude from the distal end of the protector 9 is utterly eliminated. Accordingly, an accident that a person in charge of disposal or the like might stick the needle point 41 in his or her finger or the like 1 by mistake can be prevented from occurring.

[9] Next, the wings 12a and 12b are fixed to the patient's skin by a pressure sensitive adhesive tape or the like, the closure of the tube 7 or the infusion line with the clamp is released, and supply of the infusion liquid is started.

The infusion liquid supplied from the infusion line flows through the respective inner cavities of the connector 72, the tube 7, the outer needle hub 3 and the outer needle 2, to be infused into the patient's blood vessel.

As has been described above, according to the indwelling needle assembly 1, the thumb of the hand holding the indwelling needle assembly 1 in the wing port holding mode can be prevented (or restrained), by the projected part 61, from slipping off the finger hold 54 (the proximal end of the inner needle hub 5). This permits the clinician (user) to concentrate on the intended procedure and to carry out the puncturing operation easily and safely.

In addition, since the projected part 61 is formed from the adhesive 6 for use in adhering and fixing the proximal portion of the inner needle 4 to the inner needle hub 5, the configuration is simple, and the indwelling needle assembly 1 can be manufactured without especially increasing the number of manufacturing steps.

Figure 11:
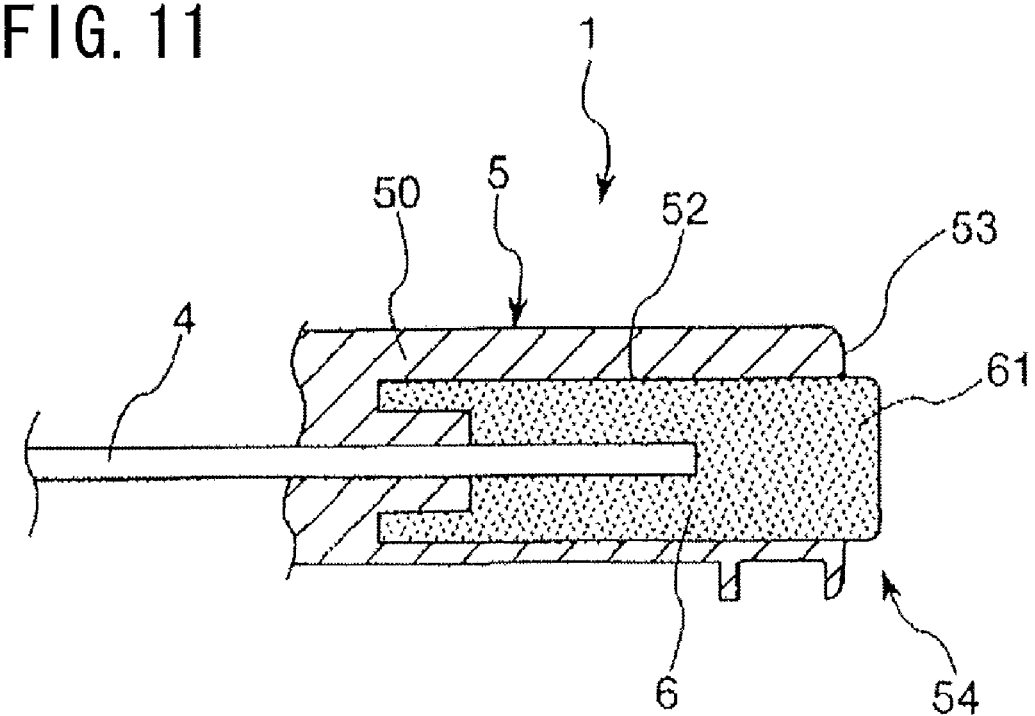
FIG. 11 is a sectional view showing another configuration example of a projected part in the indwelling needle assembly shown in FIG. 1.

Incidentally, the configuration of the projected part 61 is not limited to the above-described. For example, the projected part 61 may be protuberant (projecting in the proximal direction) from the whole area of the opening of the recess 52 of the inner needle hub body part 50, as shown in FIG. 11.

Besides, the inner needle hub 5 may be provided with a plurality of projected parts 61.

<Second Embodiment>

Figure 12A:
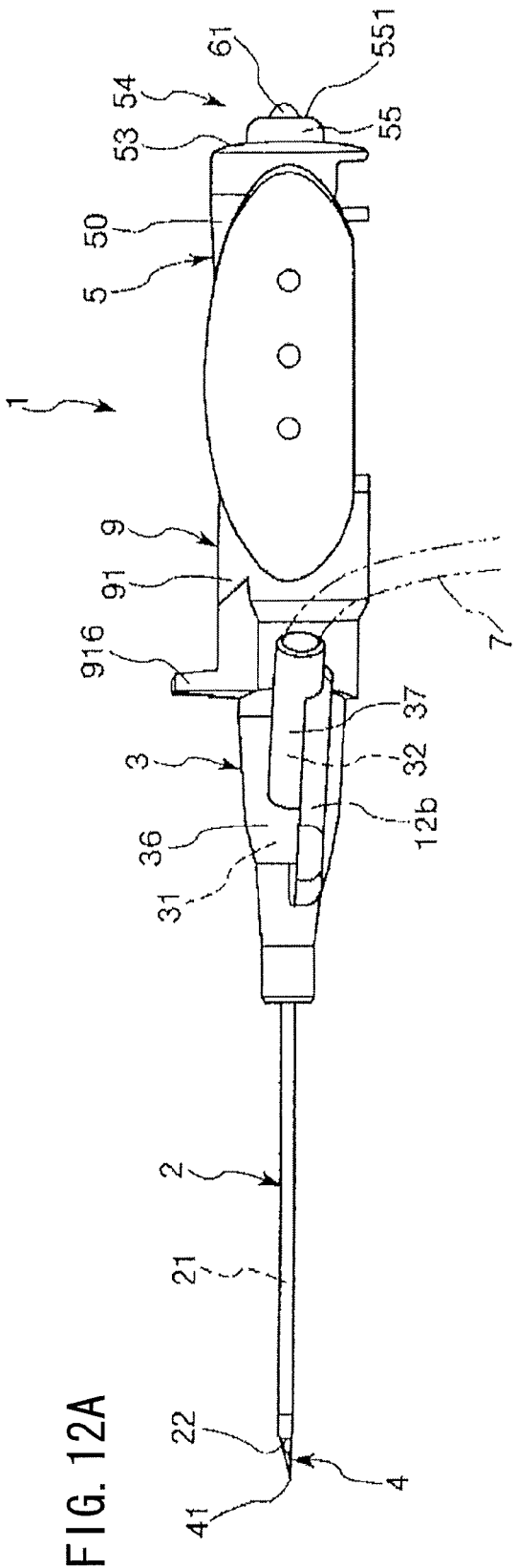
FIGS. 12A, 12B and 12C illustrate a second embodiment of the indwelling needle assembly according to the embodiment of the present invention.
Figure 12C:
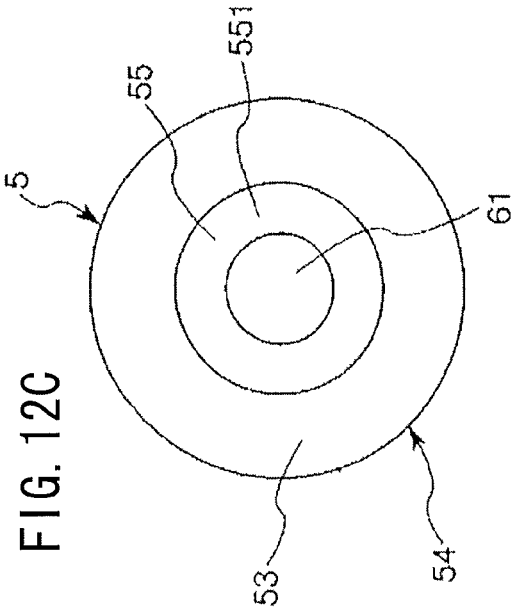
Figure 12B:
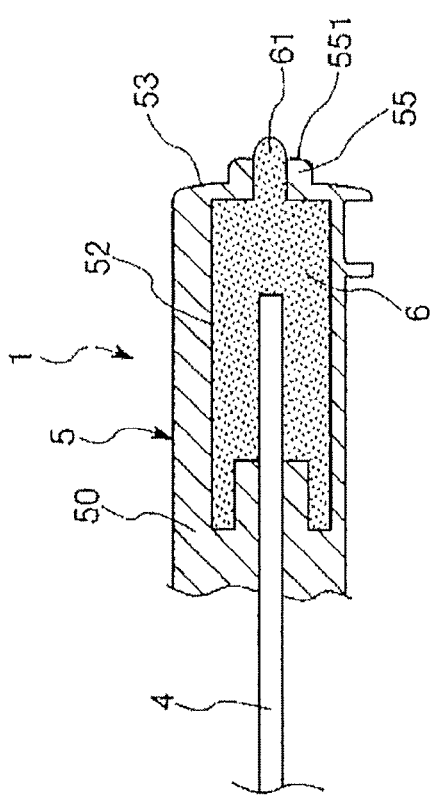

FIGS. 12A, 12B and 12C illustrate a second embodiment of the indwelling needle assembly according to the present invention, wherein FIG. 12A is a side view, FIG. 12B is a sectional view, and FIG. 12C is a rear view. Incidentally, in the following description, the left side in FIGS. 12A and 12B will be referred to as "distal," and the right side as "proximal (trailing end)."

Now, the second embodiment will be described below, mainly as to differences thereof from the first embodiment described above, and descriptions of the same items as above will be omitted.

As shown in FIGS. 12A to 12C, in the indwelling needle assembly 1 according to the second embodiment, an inner needle hub body part 50 is provided at its proximal end face 53 with an annular body 55 which projects toward the proximal side while surrounding the opening of a recess 52. A projected part 61 projects from the inside of the annular body 55 toward the proximal side relative to a proximal end face 551 of the annular body 55. Incidentally, the annular body 55 in the configuration shown in the figures is in the shape of a circular ring, as viewed along the center axis $O_1$ of the inner needle 4. A proximal end face 53 of the inner needle hub body part 50, the proximal end face 551 of the annular body 55 and the projected part 61 constitute a finger hold 54 to be contacted by the thumb of a hand holding the indwelling needle assembly 1.

In this indwelling needle assembly 1, at the time of forming the projected part 61 from an adhesive 6, the adhesive 6 can be inhibited by the annular body 55 from flowing out unwillingly. The projected part 61 can be formed by rendering the adhesive 6 protuberant in a predetermined shape and dimensions.

According to the indwelling needle assembly 1, the same effects as those of the first embodiment above can also be obtained.

While the indwelling needle assembly according to the present invention has been described above based on the embodiments shown in the drawings, the invention is not limited to the embodiments. The configurations of components can be replaced by arbitrary configurations having equivalent functions. Other arbitrary structures and/or steps may be added to the present invention.

Incidentally, the indwelling needle assembly according to the embodiment of the present invention is not limited to those which are to be used by being inserted into a blood vessel, but may also be applied, for example, to those which are to be used by being inserted into a living body such as an abdominal cavity, a thoracic cavity, a lymph vessel, a vertebral canal, etc.

Further, in the embodiment of the present invention, the protector is not limited to the one configured as shown in the drawings, insofar as it can be detachably connected to the outer needle hub. Particularly, there can be used protectors of various configurations that cover at least the needle point of the inner needle upon withdrawal of the inner needle from the outer needle.

In addition, in the embodiment of the present invention, the wings 12a and 12b may be omitted.

Besides, in the embodiment of the present invention, the side pipe 37 and/or the tube 7 can be omitted.

It should be understood by those skilled in the art that various modifications, combinations, sub-combinations and alterations may occur depending on design requirements and other factors insofar as they are within the scope of the appended claims or the equivalents thereof.

What is claimed is:

1. An indwelling needle assembly, comprising:
an inner needle having a sharp needle point at a distal end thereof;
an inner needle hub which is fixed to a proximal portion of the inner needle and which has a proximal end face;
a hollow outer needle into which the inner needle is inserted;
an outer needle hub fixed to a proximal portion of the outer needle,
wherein the inner needle is adhered and fixed to the inner needle hub with an adhesive at a proximal portion thereof, and the inner needle hub is provided with a projected part formed by projecting the adhesive toward a proximal side relative to the proximal end face; and
wherein the inner needle hub has an inner needle hub body part provided with a recess which opens toward the proximal side and which is filled with the adhesive, and the projected part is protuberant at a central portion of an opening of the recess.

2. The indwelling needle assembly according to claim 1, wherein the inner needle hub has an inner needle hub body part provided with a recess which opens toward the proximal 30 side and which is filled with the adhesive, and the projected part is protuberant from a whole area of an opening of the recess.

3. The indwelling needle assembly according to claim 1, wherein the proximal end face and the projected part of the inner needle hub constitute a finger hold to be contacted by a thumb of a hand holding the indwelling needle assembly.

4. The indwelling needle assembly according to claim 1, wherein the inner needle hub has an inner needle hub body part provided with a recess which opens toward the proximal side and which is filled with the adhesive, the inner needle hub body part is provided at a proximal end face thereof with an annular body which surrounds an opening of the recess and which projects in the proximal direction, and the projected part projects from inside the annular body toward the proximal side relative to a proximal end face of the annular body.

5. The indwelling needle assembly according to claim 1, wherein the indwelling needle assembly is used by holding it with fingers of a gloved hand.

6. The indwelling needle assembly according to claim 5, wherein the adhesive, after cured, is not slippery on the glove.

* * * * *

UNITED STATES PATENT AND TRADEMARK OFFICE
CERTIFICATE OF CORRECTION

PATENT NO. : 8,187,230 B2  
APPLICATION NO. : 12/868347  
DATED : May 29, 2012  
INVENTOR(S) : Hidenori Tanabe et al.

Page 1 of 1

It is certified that error appears in the above-identified patent and that said Letters Patent is hereby corrected as shown below:

On the Title Page, in between "(65) Prior Publication Data" information and "(51) Int. Cl.", insert the following Item --(30)    Foreign Application Priority Data

Aug. 27, 2009    (JP) ....................2009-196829--.

Signed and Sealed this  
Eighth Day of October, 2013

Teresa Stanek Rea  
*Deputy Director of the United States Patent and Trademark Office*